(12) United States Patent
Campton et al.

(10) Patent No.: US 11,119,106 B2
(45) Date of Patent: *Sep. 14, 2021

(54) ANALYTE DETECTION

(71) Applicant: RareCyte, Inc., Seattle, WA (US)

(72) Inventors: Daniel E. Campton, Seattle, WA (US);
Arturo B. Ramirez, Seattle, WA (US);
Melinda R. Duplessis, Seattle, WA (US)

(73) Assignee: RareCyte, Inc., Seattle, WA (US)

( * ) Notice: Subject to any disclaimer, the term of this patent is extended or adjusted under 35 U.S.C. 154(b) by 153 days.

This patent is subject to a terminal disclaimer.

(21) Appl. No.: 16/407,620

(22) Filed: May 9, 2019

(65) Prior Publication Data

US 2019/0310262 A1 Oct. 10, 2019

Related U.S. Application Data

(63) Continuation of application No. 15/946,498, filed on Apr. 5, 2018, now Pat. No. 10,330,684.

(51) Int. Cl.
*G01N 33/574* (2006.01)
*G01N 33/58* (2006.01)
*G01N 33/569* (2006.01)

(52) U.S. Cl.
CPC . *G01N 33/57492* (2013.01); *G01N 33/56966* (2013.01); *G01N 33/582* (2013.01)

(58) Field of Classification Search
None
See application file for complete search history.

(56) References Cited

U.S. PATENT DOCUMENTS

| | | |
|---|---|---|
| 5,244,787 A | 9/1993 | Key et al. |
| 8,067,241 B2 | 11/2011 | Gerdes et al. |
| 10,267,805 B1 | 4/2019 | Campton et al. |
| 10,274,498 B1 | 4/2019 | Campton et al. |
| 10,330,684 B1 | 6/2019 | Campton et al. |
| 2005/0079606 A1 | 4/2005 | Tarnaki et al. |
| 2011/0171652 A1 | 7/2011 | You |
| 2017/0166869 A1 | 6/2017 | Gonzalez |

FOREIGN PATENT DOCUMENTS

| | | |
|---|---|---|
| WO | WO2008063378 A2 | 5/2008 |
| WO | WO2009110936 A2 | 9/2009 |
| WO | WO2010028277 A1 | 3/2010 |
| WO | WO2014138183 A1 | 9/2014 |

OTHER PUBLICATIONS

Wakayama et al. (J. Histochem Cytochem 2015 vol. 63, p. 190-205 (Year: 2015).*
Naito et al. (Med Electron Microsc 2003 vol. 36, p. 1-7) (Year: 2003).*
Oliver et al.; Immunocytochemical Methods and Protocols; Third Edition; 6 pgs; 2010.
Myers; Overview of Heat-Induced Epitope Retrieval (HIER) Techniques and Devices; 5 pages; retrieved from the internet (http://www.ihcworld.com/_protocols/epitope_retrieval/overview.htm) or Sep. 18, 2018.
Campton et al.; High-Recovery Visual Identification and Single-Cell Reteieval of Circulating Tumor Cells for Genomic Analysis Using a Dual-Technology Platform Integrated with Automated Immunofluorescence Staining; BMC Cancer; 15(360); 13 pgs; 2015.
Wang et al.; Quantum Dots-Based Tissue and In Vivo imaging in Breast Cancer Researches: Current Status and Future Perspectives; Breast Cancer Res Treat; 151; pp. 7-17; 2015.
Chen et al.; Capture and identification of heterogeneous circulating tumor cells using transparent nonmaterials and quantum dots-based multiplexed imaging; J. Cancer; 2016; (7)1: 69-79.
Yamashita et al.; Heat-induced antigen retrieval in conventionally processed epon-embedded specimens: procedures and mechanisms; J. Histochem. Cytochem.; 62(8); pp. 584-597; 2014.
Emoto et al.; Mechanisms of heat-induced antigen retrieval: does pH or ionic strength of the solution play a role for refolding antigens?; J. Histochem. Cytochem.; 53(11); pp. 1311-1321; 2005.
Yu et al.; identification of blood vascular endothelial stem cells by the expression of protein C receptor; Cell Research (26); pp. 1079-1098; Jul. 1, 2016.

* cited by examiner

*Primary Examiner* — Changhwa J Cheu
(74) *Attorney, Agent, or Firm* — Shay Glenn LLP

(57) ABSTRACT

This disclosure relates generally to detection and, in particular, to detecting objects within a sample or fraction thereof.

27 Claims, 2 Drawing Sheets

ANALYTE DETECTION

CROSS REFERENCE TO RELATED APPLICATIONS

This application is a continuation of U.S. application Ser. No. 15/946,498, filed Apr. 5, 2018.

FIELD

This disclosure relates generally to detection and, in particular, to detecting objects within a sample or fraction thereof.

BACKGROUND

Samples often include objects that are to be imaged for analysis. These objects may include a plurality of biomarkers and/or components for which it is desirous to detect and image. As a result, practitioners, researchers, and those working with samples continue to seek systems and methods to more efficiently and accurately detect and image objects of a sample.

DETAILED DESCRIPTION

Figure 1:
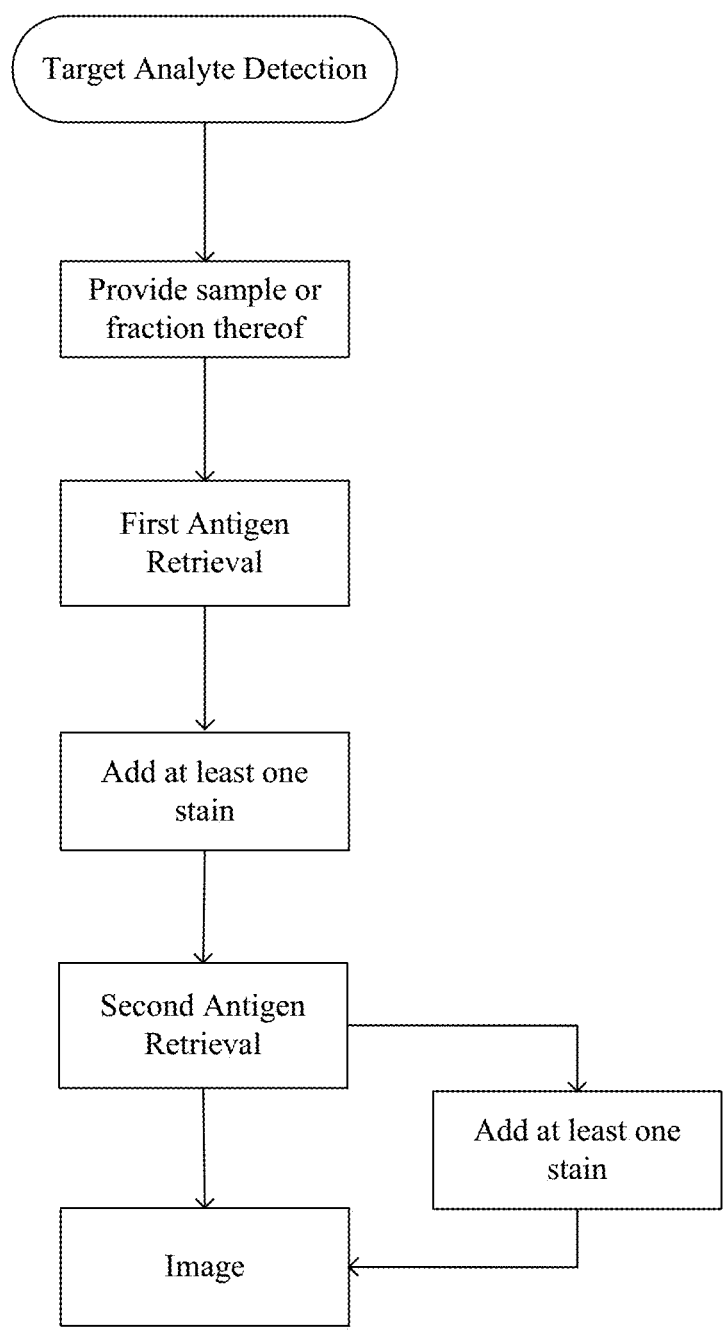
FIG. 1 shows an example method including two antigen retrieval steps.

In the following descriptions, the term "light" is used to describe various uses and aspects of multiplexing and imaging. The term light is not intended to be limited to describing electromagnetic radiation in the visible portion of the electromagnetic spectrum, but is also intended to describe radiation in the ultraviolet and infrared portions of the electromagnetic spectrum.

In the following descriptions, the term "sample" is used to describe a biological fluid, a biological semi-solid, a biological solid (which may remain solid, such as tissue, or may be liquefied in any appropriate manner), a suspension, a portion of the suspension, a component of the suspension, or the like. For example, for anticoagulated whole blood, the sample is the anticoagulated whole blood (i.e. a suspension), the buffy coat (i.e. a portion of the suspension), or a circulating tumor cell (i.e. a component of the suspension). For the sake of convenience, the sample referenced is whole blood, though it should be understood that the method and system described and discussed herein is used with any appropriate sample, such as urine, blood, bone marrow, buffy coat, cystic fluid, ascites fluid, stool, semen, cerebrospinal fluid, nipple aspirate fluid, saliva, amniotic fluid, mucus membrane secretions, aqueous humor, vitreous humor, vomit, vaginal fluid, and any other physiological fluid or semi-solid. For example, the sample is a tissue sample or a material from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, or a bladder.

In the following descriptions, the terms "target analyte" or "target material" are used to describe a biological material of interest. It should also be understood that the target analyte can be a fraction of a sample, such as buffy coat, a cell, such as ova, fetal material (such as trophoblasts, nucleated red blood cells, fetal red blood cells, fetal white blood cells, fetal DNA, fetal RNA, or the like), a circulating tumor cell ("CTC"), a circulating endothelial cell, an immune cell (i.e. naïve or memory B cells or naïve or memory T cells), a mesenchymal cell, a stem cell, a vesicle, such as an exosome, a liposome, a protein, a nucleic acid, a biological molecule, a naturally occurring or artificially prepared microscopic unit having an enclosed membrane, parasites (e.g. spirochetes, such as *Borrelia burgdorferi* which cause Lyme disease; malaria-inducing agents), microorganisms, viruses, or inflammatory cells. For example, the target analyte is a tumor cell from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, or a bladder.

In the following descriptions, the term "non-target analyte" is used to describe a biological material which is not a target analyte.

In the following descriptions, the term "biomarker" is used to describe a substance that is present on or within the target analyte or target material (i.e. intracellular or extracellular the target analyte; internalized, such as through phagocytosis, within the target analyte; or the like). Biomarkers include, but are not limited to, peptides, proteins, subunits, domains, motifs, epitopes, isoforms, DNA, RNA, or the like. The biomarker may be a target molecule for drug delivery.

In the following descriptions, the term "affinity molecule" is used to describe any molecule that is capable of binding or interacting with a biomarker. The interaction or binding can be covalent or non-covalent. The affinity molecule includes, but is not limited to, an antibody, a hapten, a protein, an aptamer, an oligonucleotide, a polynucleotide, or any appropriate molecule for interacting with or binding to the biomarker.

In the following descriptions, the term "detection moiety" is used to describe a compound or substance which provides a signal for detection, thereby indicating the presence of another compound or substance, an analyte, or the like within a sample or specimen. The detection moiety can be fluorescent, such as a fluorescent probe, or chromogenic, such as a chromogenic dye.

In the following descriptions, the term "channel" is used to describe a color or color range based on the signal provided by one or more detection moieties. The color or color range is obtained based on the filters chosen and/or the wavelength of the signal(s). For example, a channel may be violet, blue, green, yellow, orange, red, dark red, or the like. Furthermore, when a plurality of channels are used, each channel has a specific color or color range. For example, a first channel may be green and a second channel may be orange. It should be noted that although two or more detection moieties may provide signals having different wavelengths, the signals can be in the same channel based on the filter set used. For example, a first detection moiety provides signal having a wavelength of 488 and a second detection moiety provides a signal having a wavelength of 500. Even though the wavelengths are not identical, the filter set in one of the channels passes wavelengths of both 488 nm and 500 nm, which permits both to be imaged at the same time, thereby producing a single image including the 488 and 500 emissions.

In the following descriptions, the terms "stain" or "label," which are used interchangeably, are used to describe an affinity molecule bound to or interacted with a detection moiety. The binding or interaction can be direct or indirect. Direct binding or interaction includes covalent or non-covalent interactions between the biomarker and the detection moiety. Indirect binding or interaction includes the use of at least first and second complementary molecules which form binding pairs. The first and second complementary molecules are, in combination, binding pairs which binds or interacts in at least one of the following manners: hydrophobic interactions, ionic interactions, hydrogen bonding interactions, non-covalent interactions, covalent interactions, affinity interactions, or the like. The binding pairs include, but are not limited to, immune-type binding-pairs, such as, antigen-antibody, antigen-antibody fragment, hapten-anti-hapten, or primary antibody-secondary antibody; nonimmune-type binding-pairs, such as biotin-avidin, biotin-streptavidin, folic acid-folate binding protein, hormone-hormone receptor, lectin-specific carbohydrate, enzyme-enzyme, enzyme-substrate, enzyme-substrate analog, enzyme-pseudo-substrate (substrate analogs that cannot be catalyzed by the enzymatic activity), enzyme-cofactor, enzyme-modulator, enzyme-inhibitor, or vitamin B12-intrinsic factor. Other suitable examples of binding pairs include complementary nucleic acid fragments (including complementary nucleotides, oligonucleotides, or polynucleotides); Protein A-antibody; Protein G-antibody; nucleic acid-nucleic acid binding protein; polymeric linkers (e.g., polyethylene glycol); or polynucleotide-polynucleotide binding protein. The binding pairs can be included within or used as amplification techniques. Amplification techniques are also implemented to increase the number of detection moieties bound to or interacted with the biomarker to increase a signal. In one embodiment, when binding pairs are used, the stain can be pre-conjugated, such that, during a labeling, staining, or adding step, the affinity molecule is already bound to or interacted with a detection moiety when added to the sample. In one embodiment, when binding pairs are used, the stain can be conjugated in the sample, such that the labeling, staining, or adding step includes at least two sub-steps including introducing (in any desired or appropriate order) an affinity molecule-first binding molecule conjugate and a second binding pair molecule-detection moiety conjugate, wherein the first and second binding pair molecules are complementary and bind to or interact with each other.

Furthermore, "a plurality of stains" can be used to describe two or more stains in which the affinity molecules and/or the detection moieties are different. For example, anti-CK-Alexa 647 is different than anti-EpCAM-Alexa 647. As another example, anti-CK-Alexa 647 is different than anti-CK-Alexa 488.

In the following descriptions, the terms "permeabilize" or "permeabilization" are used to describe the dissolution or removal of a portion of a plasma membrane of a target or non-target analyte by chemical or other means, such that at least an IgG antibody is capable of crossing the plasma membrane.

In the following descriptions, the term "conjugate" is used to describe a first chemical, molecule, moiety, or the like bound to or interacted with a second chemical, molecule, moiety, or the like. The binding or interaction is direct or indirect. Direct binding or interaction includes covalent or non-covalent interactions between the biomarker and the detection moiety. Indirect binding or interaction includes the use of at least first and second complementary molecules which form binding pairs. The first and second complementary molecules are, in combination, binding pairs which binds or interacts in at least one of the following manners: hydrophobic interactions, ionic interactions, hydrogen bonding interactions, non-covalent interactions, covalent interactions, affinity interactions, or the like. The binding pairs include, but are not limited to, immune-type binding-pairs, such as, antigen-antibody, antigen-antibody fragment, hapten-anti-hapten, or primary antibody-secondary antibody; nonimmune-type binding-pairs, such as biotin-avidin, biotin-streptavidin, folic acid-folate binding protein, hormone-hormone receptor, lectin-specific carbohydrate, enzyme-enzyme, enzyme-substrate, enzyme-substrate analog, enzyme-pseudo-substrate (substrate analogs that cannot be catalyzed by the enzymatic activity), enzyme-cofactor, enzyme-modulator, enzyme-inhibitor, or vitamin B12-intrinsic factor. Other suitable examples of binding pairs include complementary nucleic acid fragments (including complementary nucleotides, oligonucleotides, or polynucleotides); Protein A-antibody; Protein G-antibody; nucleic acid-nucleic acid binding protein; polymeric linkers (e.g., polyethylene glycol); or polynucleotide-polynucleotide binding protein.

General Method

An example method for labeling a biomarker on a target analyte is discussed. In one embodiment, a sample, such as blood, is obtained, such as by venipuncture. The sample is suspected of including at least one target analyte. Suitable devices, systems, and/or methods of sample collection and/or processing may include those described in one or more of the following U.S. patents and published applications, each of which is hereby incorporated by reference in its entirety: U.S. Pat. Nos. 7,074,577; 7,220,593; 7,329,534; 7,358,095; 7,629,176; 7,915,029; 7,919,049; 8,012,742; 9,039,999; 9,217,697; 9,492,819; 9,513,291; 9,533,303; 9,539,570; 9,541,481; 9,625,360; 2014/0161688; 2017/0014819; 2017/0059552; 2017/0074759. Suitable devices, systems, and/or methods for target analyte retrieval, isolation, or picking may include those described in one or more of the following U.S. patents and published applications, each of which is hereby incorporated by reference in its entirety: U.S. Pat. Nos. 9,222,953; 9,440,234; 9,519,002; 9,810,605; 2017/0219463; 2017/0276575.

The sample is then dispensed onto or into at least one analysis platform. The analysis platform is a microscope slide, a positively charged microscope slide, a negatively charged microscope slide, a coated microscope slide, a porous slide, a micro-well slide, a well plate, a coverslip, a cell microarray, or the like. The analysis platform can be any appropriate material, including, but not limited to, glass, plastic, ceramic, metal, or the like.

In one embodiment, the sample is re-suspended in an attachment solution in a vessel prior to being dispensed onto the analysis platform. For example, the attachment solution is added to or mixed with the sample. The re-suspended sample, which includes at least a portion of the attachment solution is dispensed onto or into the analysis platform by a dispenser, such as a pipet or repeating pipet. In one embodiment, the attachment solution includes an alcohol (such as ethanol or methanol) and a non-steroidal anti-inflammatory drug (such as aspirin). In one embodiment, the attachment solution includes an alcohol (such as ethanol or methanol) and an anti-coagulant (such as heparin). In one embodiment, the attachment solution includes an alcohol (such as ethanol or methanol), an anti-coagulant (such as heparin), and a non-steroidal anti-inflammatory drug (such as aspirin).

In one embodiment, the sample is spread across the analysis platform. In one embodiment, the sample is spread across the analysis platform by a spreader, such as a squeegee, a pipet tip, a blade, a two-piece spreader including a blade and a base. In one embodiment, the sample is spread across the analysis platform by centrifuging, wetting, or nutating the analysis platform.

In one embodiment, the re-suspended sample is cured to adhere the re-suspended sample to the analysis platform. In one embodiment, the re-suspended sample is dispensed onto the analysis platform and cured without being spread across the analysis platform. Curing occurs in air, such as at room temperature; in an environmentally-controlled chamber, such as at 37° C.; or the like. Furthermore, the sample may undergo an additional fixation step, such as in treatment with formalin or any appropriate fixative, after the curing step has been completed.

In one embodiment, at any point prior to staining, autofluorescence is reduced or eliminated. The autofluorescence is reduced or eliminated by bleaching the sample with a chemical (such as hydrogen peroxide), an enzyme, light, heat, or the like.

The sample then undergoes staining. At least one stain is added to the sample for labeling, such as by an autostainer or manually by an operator. In one embodiment, the at least one target analyte is stained. In one embodiment, at least one non-target analyte or non-target material is stained. In one embodiment, the at least one target analyte and the at least one non-target analyte or materials are stained.

The biomarker or biomarkers include, but are not limited to: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD31, CD32, CD33 (p67 proteins), CD34, CD38, CD40, CD40L, CD44, CD45, CD46, CD49a, CD52, CD54, CD55, CD56, CD61, CD64, CD66b, CD66e, CD74, CD80 (B7-1), CD89, CD95, CD105, CD123, CD137, CD138, CD140a, CD144, CD146, CD147, CD148, CD152, CD164, CEACAM5, CFTR, cGMP, CINC, *Clostridium botulinum* toxin, *Clostridium peffringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin, DAN, DCC, DcR3, DC-SIGN, Decay accelerating factor, des(1-3)-IGF-I (brain IGF-1), Dhh, digoxin, DLL3, DNAM-1, Dnase, Dpp, DPPIV/CD26, Dtk, EGAD, EDA, EDA-A1, EDA-A2, EDAR, EGF, EGFR (ErbB-1), EMA, EMMPRIN, ENA, endothelin receptor, ER, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), fibronectin, Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-1, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), Ki67, laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MPIF, Mpo, M30, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3,-4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PR, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, 5100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta R11, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFa, TNF-RI, TNF-RII, TNFRSF10A (TRAIL R1 Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITRAITR), TNFRSF19 (TROY TAJ, TRADE), TNFRSF19L (RELT), TNFRSF1A (TNF R1CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1 BB CD137, ILA), TNFRSF21 (DR6), TNFRSF22 (DCTRAIL R2TNFRH2), TNFRST23 (DCTRAIL R1 TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1 B (TNF-b LTa, TNFSF1), TNFSF3 (LTb TNFC, p33), TNFSF4 (0X40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Vimentin, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors. The biomarkers include proteins, subunits, domains, motifs, isoforms, and/or epitopes belonging to the list above.

The detection moiety is a compound or substance which provides a signal for detection, thereby indicating the presence of another compound or substance, an analyte, or the like within a sample or specimen. The detection moiety can be used as a tracer, as a label for certain structures, as a label for biomarkers, or the like. The detection moiety can be distributed or can label the appropriate structure or biomarkers in manners including, but not limited to, uptake, selective uptake, diffusion, and attachment to a linking molecule. The detection moiety is bound to the biomarker via an affinity molecule (i.e. an antibody capable of binding or interacting with the biomarker; or, "direct labeling") or to the biomarker via an affinity molecule and at least one linking molecules extending from the affinity molecule to the detection moiety (i.e. "indirect labeling").

The detection moiety can be fluorescent, such as a fluorescent probe, or chromogenic, such as a chromogenic dye. The chromogenic dye, which can be used with various enzyme labels (e.g. horseradish peroxidase and alkaline phosphate), includes, but is not limited to, 3,3'-Diaminobenzidine (DAB), 3-Amino-9-Ethylcarbazole (AEC), 4-Chloro-1-Naphtol (CN), P-Phenylenediamine Dihydrochloride/pyrocatechol (Hanker-Yates reagent), Fast Red TR, New Fuchsin, Fast Blue BB, or the like. The fluorescent probe can be a reactive dye, an organic dye, a fluorescent protein, a quantum dot, non-protein organic molecules, a nanoparticle (e.g., nanodiamond), or the like. Fluorescent probes include, but are not limited to 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; AB Q; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AutoFluorescent Protein; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9(Bisaminophenyloxadiazole); BCECF (high pH); BCECF (low pH); Berberine Sulphate; Beta Lactamase; BFP blue shifted GFP (Y66H; Blue Fluorescent Protein); BFP/GFP FRET; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Brilliant Violet 421; Brilliant Violet 510; Brilliant Violet 605; Brilliant Violet 650; Brilliant Violet 711; Brilliant Violet 786; BTC; BTC-5N; Calcein; Calcein Blue; Calcium Crimson™; Calcium Green; Calcium Green-1; Calcium Green-2; Calcium Green-5N; Calcium Green-C18; Calcium Orange; Calcofluor White; Carboxy-X-hodamine (5-ROX); Cascade Blue™; Cascade Yellow; Catecholamine; CCF2 (GeneBlazer); CFDA; CFP (Cyan Fluorescent Protein); CF405S; CF488A; CF 488; CF 543; CF 647; CF 750; CF 760; CF 780; FP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); CyQuant Cell Proliferation Assay; Dabcyl; Dansyl; Dansyl Amine; Dansyl Cadaverine; Dansyl Chloride; Dansyl DHPE; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS; DiA (4-Di-16-ASP); Dichlorodihydrofluorescein Diacetate (DCFH); DiD-Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DM-NERF (high pH); DNP; Dopamine; DsRed; DTAF; DY-630-NHS; DY-635-NHS; EBFP (Enhanced Blue Fluorescent Protein); ECFP (Enhanced Cyan Fluorescent Protein); EGFP(Enhanced Green Fluorescent Protein); ELF 97; Eosin; ER-Tracker™ Green; ER-Tracker™ Red; ER-Tracker™ Blue-White DPX; Erythrosin; Erythrosin ITC; Ethidium Bromide; Ethidium homodimer-1 (EthD-1); Euchrysin; EukoLight; Europium (III) chloride; EYFP (Enhanced Yellow Fluorescent Protein); Fast Blue; FDA; FIF (Formaldehyde Induced Fluorescence); FITC; FITC Antibody; Flazo Orange; Fluo-3; Fluo-4; Fluorescein (FITC); Fluorescein Diacetate; FluoroEmerald; Fluoro-Gold (Hydroxystilbamidine); Fluor-Ruby; FluorX; FM 1-43™; FM 4-46; Fura Red™ (high pH); Fura Red™/Fluo-3; Fura-2, high calcium; Fura-2, low calcium; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green; Mitotracker Orange; Mitotracker Red; Mitramycin; Monobromobimane; Monobromobimane (mBBr-GSH); Monochlorobimane; MPS (Methyl Green Pyronine Stilbene); mStrawberry; NBD; NBD Amine; Nile Red; Nitrobenzoxadidole; Noradrenaline; Nuclear Fast Red; Nuclear Yellow; Nylosan Brilliant lavin EBG; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B; Phycoerythrin R; PKH26 (Sigma); PKH67; PMIA; Pontochrome Blue Black; POPO-1; POPO-3; PO-PRO-1; PO-PRO-3; Primuline; Procion Yellow; Propidium Iodid (PI); Pyrene; Pyronine; Pyronine B; Pyrozal Brilliant Flavin 7GF; QD500; QD525; QD625; QD800; QSY 7; Quinacrine Mustard; Red 613 (PE-TexasRed); Resorufin; RFP; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin; rsGFP (red shifted GFP (S65T)); S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgGFP™ (super glow GFP; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; SYTOX Red; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; Tri-Color (PE-Cy5); TetramethylRodamineIsoThioCyanate; True Blue; TruRed; Tubulin Tracker™ Green; Ultralite; Uranine B; Uvitex SFC; wt GFP (wild type GFP); WW 781; X-Rhodamine; XRITC; Xylene Orange; Y66F; Y66H; Y66W; Yellow GFP (Yellow shifted); Green Fluorescent Protein; YFP (Yellow Fluorescent Protein); YO-PRO-1; YO-PRO-3; YOYO-1; YOYO-3; and, combinations and derivatives thereof. In one embodiment, the detection moiety, such as organic fluorophore, can have a molecule weight of at least 1 kD, including, without limitation, at least 10 kD, at least 25 kD, at least 50 kD, at least 75 kD, at least 100 kD, at least 150 kD, at least 200 kD, at least 250 kD, at least 300 kD, at least 340 kD, at least 350 kD, at least 500 kD, and at least 750 kD.

It should be noted that a nuclear stain, such as Sytox, may be used in combination with a quantum dot. In one embodiment, the quantum dot has an emission peak less than or equal to 520 nm. In one embodiment, the quantum dot has an emission peak greater than or equal to 520 nm.

After labeling, the sample is imaged, whereby the sample is illuminated with one or more wavelengths of excitation light from a light source, such as infrared, red, blue, green, and/or ultraviolet. The imaging can be done with a flow cytometer or a microscope, such as a fluorescent microscope, a scanner, or the like. Imaging can be done in brightfield and/or darkfield illumination, phase contrast, differential interference contrast, fluorescence, light sheet microscopy, super resolution microscopy, confocal microscopy, and Hoffman modulation contrast. The images formed can be overlaid when a plurality of detection moieties are used. Emission, reflection, diffraction, scatter, and combinations thereof are used in for detection/imaging. The images are analyzed to detect, enumerate, and locate the target analyte. Imaging is performed in a tube, on a microscope slide, or in any appropriate vessel or substrate for imaging.

The target analyte can be retrieved from the rest of the sample. To retrieve the target analyte, the target analyte undergoes enrichment and/or isolation. The target analyte is isolated from rest of the sample, whether with or without prior enrichment, by selecting the target analyte at a time with any appropriate device or system. Imaging the analysis platform, as discussed above, is performed to aid in isolation by providing location and characterization information for isolation purposes.

The target analyte can undergo post-processing analysis, such as sequencing, by using any appropriate method or technique, though more specifically extracellular and intracellular analysis including intracellular protein labeling; nucleic acid analysis, including, but not limited to, DNA arrays, expression arrays, protein arrays, and DNA hybridization arrays; or in situ hybridization ("ISH"—a tool for analyzing DNA and/or RNA, such as gene copy number changes); polymerase chain reaction ("PCR"); reverse transcription PCR. Sequencing is done on the entire genome, the transcriptome, or cDNA.

The steps of the method described above can be performed by at least one of an imaging microscope, a scanner, a flow cytometer, or a microfluidic device, such as a chip or a microchannel, or the method can be performed by any combination of the above. For example, the flow cytometer is used for the collecting step, where enrichment via fluorescent-activated cell sorting is appropriate, and the microfluidic device is used for the retrieving step. In other words, the methods, though described to include one device per method, may be performed such that a combination of devices are used. The devices are capable of being used in any appropriate transmitted light modality. The devices are capable of being used in at least one of brightfield and/or darkfield illumination, phase contrast, differential interference contrast, fluorescence, and Hoffman modulation contrast imaging or detection.

In one embodiment, the patient sample is a fraction of a suspension, such that the sample is obtained through enrichment, including positive and/or negative enrichment and/or density-based enrichment. The enriched fraction is suspected of including at least one target analyte. The sample is enriched by any appropriate enrichment process including, but not limited to, sequential density fractionation, magnetic-activated cell sorting, fluorescence-activated cell sorting, differential lysis, depletion filters, microfluidic device separation, or the like. Sequential density fractionation is a process by which a patient sample is divided into fractions or a fraction of a sample is divided into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, separation fluids are used whereby each separation fluid has a different density, thereby separating a fraction of a sample into sub-fractions based on the densities of the respective sub-fractions via the different density separating fluids.

Multiplexing

Though "a biomarker" is discussed, any number of biomarkers can be labeled for multiplexing purposes, which allows, for example, multiple biomarkers to be identified using a single image. For example, it can be desirous to detect more than one biomarker of a given target analyte. A set of stains, which includes at least two stains and can include up to 4, 6, 8, 10, or more, is used to multiplex the target analyte, such that each stain labels a different biomarker of the target analyte. This allows for detection of a plurality of biomarkers on the target material at any given time. In one embodiment, a plurality of detection moieties is used. For example, Alexa 488 and Alex 647 are used. In one embodiment, a plurality of types of detection moieties are used. For example, Alexa 488 and QD800 are used. In one embodiment, a plurality of detection moieties and a plurality of types of detection moieties are used. In one embodiment, at least two stains are in the same channel and at least one stain is in at least one other channel.

Furthermore, the types of affinity molecules used are selected based on the desired characteristics of the target analyte or in trying to determine a particular characteristic of the target analyte. For example, mesenchymal, epithelial, and confirmatory/characterization (i.e. cancer cell type (e.g., prostate, breast, colon, lung, etc.)) affinity molecules can be selected to characterize a given target analyte into various cell types. In one embodiment, a plurality of affinity molecules (i.e. first and second affinity molecules) is selected to bind to or interact with a plurality of biomarkers of the target analyte, where each of the plurality of affinity molecules is: (1) directed to a different biomarker of the target analyte; and (2) bound to detection moieties which provide signals in different channels. The detection moieties may be the same or different types. Accordingly, any number of affinity molecules and corresponding detection moieties are implemented whereby the complementary molecules or complexes are specific to each other. For example, an EpCAM antibody is selected as the first affinity molecule to bind or interact with an EpCAM biomarker of the target analyte, and a HER2 antibody is selected as the second affinity molecule to bind or interact with a HER2 biomarker of the target analyte. The EpCAM antibody is bound to or interacted with a first detection moiety and the HER2 antibody is bound to or interacted with a second detection moiety, such that the first and second detection moieties emit in a different channel.

In one embodiment, a plurality of affinity molecules (i.e. first and second affinity molecules) is selected to bind to or interact with a plurality of biomarkers on the target analyte, where each of the plurality of affinity molecules is: (1) directed to a different biomarker of the target analyte; and (2) bound to detection moieties which provide a signal in the same channel. The detection moieties of the first and second affinity molecules may be the same or may be different but provide signals within the same channel. For example, an EpCAM antibody is selected as the first affinity molecule to bind or interact with an EpCAM biomarker of the target analyte, and a cytokeratin antibody is selected as the second affinity molecule to bind or interact with a cytokeratin biomarker of the target analyte. The EpCAM antibody and the cytokeratin antibody are bound to detection moieties which provide a signal in, for example, the green channel.

In one embodiment, (1) a plurality of affinity molecules (i.e. first and second affinity molecules) is selected to bind to or interact with a plurality of biomarkers on the target analyte, where each of the plurality of affinity molecules is: (a) directed to a different biomarker of the target analyte, and (b) bound to the same type of detection moiety; and (2) at least one affinity molecule (i.e. a third affinity molecule) is selected to bind to or interact with a third biomarker and is bound to a different type of detection moiety. For example, the detection moieties bound to or interacted with the first and second affinity molecules provide signals within the same channel, whereas the detection moiety bound to or interacted with the third affinity molecules provides a signal in a different channel.

In one embodiment, a plurality of stains can be used such that each stain includes a different binding pair. In one embodiment, a plurality of stains can be used such that at least stains include the same binding pair.

Cyclic Labeling

In one embodiment, multiple rounds of labeling is performed for cyclic labeling purposes. For example, a target analyte is labeled with a first set of labels, the first set of labels are imaged, the signal provided by the stains are reduced or eliminated (such as with heat (between 50-110° C., including 70° C., 80° C., 90° C., 95° C., 100° C., or 105° C.), light, chemicals, enzymes, higher affinity molecules to remove the detection moiety, or any appropriate manner in which to reduce or eliminate the signal, such as by degrading, cleaving, or modifying), the target analyte is labeled with a second set of labels, and so on until a desired number of biomarkers have been labeled and/or a desired number of rounds have been performed. The heating step is performed in any device or system appropriate for heating the sample, including, but not limited to, an autostainer, a steamer (such as a vegetable steamer or a bottle sanitizer), a pressure cooker, an autoclave, a water bath, a hot plate, a crockpot, a hair dryer, an incubator, a microwave, or a combination thereof.

In one embodiment, a single stain is used for each round of labeling, such that five stains are used individually across five rounds of labeling. In one embodiment, a plurality of stains is used for each round of labeling, such that each round of labeling uses a plurality of stains. In one embodiment, at least one round of labeling includes a plurality of stains and at least one round of labeling includes a single stain.

Amplification

In one embodiment, amplification techniques are used to increase the signal-to-noise ratio within at least one channel or for at least one stain. The amplification techniques include, but are not limited to, addition of amplification moieties such as haptens and anti-haptens (such as DNP and anti-DNP; DIG and anti-DIG; FITC and anti-FITC; HQ and anti-HQ; and biotin), primary and secondary antibodies, horseradish peroxidase (HRP) and tyramide, HRP or alkaline phosphatase and 3,3' diaminobenzidine (DAB) or 3-amino-9-ethylcarbazole (AEC), and complementary molecules (such as biotin and an avidin). These amplification moieties bind to or interact with affinity molecules, whether directly or indirectly, that are themselves bound to or have interacted with one or more biomarkers.

In one embodiment, amplification is performed on a single biomarker. In one embodiment, amplification is performed on two or more biomarkers. In one embodiment, amplification performed on two or more biomarkers uses different types of amplification techniques. In one embodiment, amplification performed on two or more biomarkers uses the same type of amplification technique. For example, tyramide signal amplification, which includes at least one horseradish peroxidase molecule (which can be directly or indirectly bound to or interacted with the affinity molecule bound to or interacted with the biomarker) and at least one tyramide-detection moiety conjugate, can be used to amplify multiple biomarkers, whether they are in the same channel or a different channel. Additionally, multiple haptens can be used to amplify multiple biomarkers, whether they are in the same channel or a different channel. When using multiple haptens, the same type of haptens can be used to amplify different biomarkers; different types of haptens can be used to amplify different biomarkers; or two or more biomarkers may be amplified by a first type of hapten and one or more biomarkers may be amplified by a second type of hapten.

In one embodiment, an amplification moiety (e.g., HRP) denaturing step can be implemented, such as by adding hydrogen peroxide. The amplification moiety denaturing step eliminates potential cross-reactivity of affinity molecules while allowing for the amplification of a species-independent channel. In other words, the amplification moiety denaturing step opens up an imaging channel for detection of an additional biomarker. In one embodiment, the amplification moiety denaturing step is performed before an antigen retrieval step, such as the second antigen retrieval step when two antigen retrievals are performed. In one embodiment, the amplification moiety denaturing step is performed after an antigen retrieval step, such as the second antigen retrieval step when two antigen retrievals are performed. The species of that affinity molecule can be independent of any other species implemented in another channel. Species, for example, include, but are not limited to a cat, chicken, cow, dog, donkey, goat, guinea pig, hamster, horse, human, llama, monkey, mouse, pig, rabbit, rat, or sheep.

Antigen Retrieval

Antigen retrieval is a process by which epitope detectability on a sample is increased. During antigen retrieval, the sample is incubated with a solution, such as a buffer (e.g., tris-based buffer, Cell Conditioning 1 from Ventana, or the like), for a given amount of time (e.g., 1 min to 24 hours, including, without limitation, 2 min, 3 min, 4 min, 5 min, 10 min, 15 min, 20 min, 30 min, 45 min, 60 min, 2 hours, 3 hours, 4 hours, 6 hours, 8 hours, 10 hours, 12 hours, and 18 hours) at a given temperature (50-110° C., including at 50-90° C., 50-85° C., 60-80° C., 65-85° C., 70° C., 80° C., 85° C., or at 90° C.). The time and temperature are selected based on the desired epitope or biomarker to be retrieved and appropriate conditions for renaturing the desired epitope or biomarker. Antigen retrieval unmasks epitopes that otherwise would not be detectable to a specific antibody due to sample processing, such as fixation.

In one embodiment, antigen retrieval is implemented a single time. In one embodiment, multiple antigen retrievals (e.g., 2, 3, 4, 5, up to 10, up to 25, up to 50, up to 100, or any desirable or appropriate amount) can be performed. In one embodiment, when multiple antigen retrievals are performed, each successive antigen retrievals can use a higher temperature than the previous antigen retrievals. In one embodiment, when multiple antigen retrievals are performed, each successive antigen retrievals can use a lower temperature than the previous antigen retrievals. In one embodiment, when multiple antigen retrievals are performed, successive antigen retrievals can use a higher or lower temperature than the previous antigen retrieval based on the appropriate conditions for antigen retrieval of the desired or targeted epitope/biomarker.

In one embodiment, and as seen in FIG. 1, at least two separate antigen retrievals can be implemented to prevent a reduction or elimination of efficacy of an antibody, detection moiety, reagent, or the like (such as by denaturing), where a particular condition (such as temperature) affects the efficacy of the antibody, detection moiety, reagent, or the like. A first antigen retrieval is performed at approximately 50-110° C., including at 50-90° C., 50-85° C., 60-80° C., 65-85° C., 70° C., 80° C., 85° C., or at 90° C. The first antigen retrieval step is performed on or for an epitope or biomarker which can be denatured or have its detectability reduced when exposed to an antigen retrieval step above a given temperature. Labeling of at least one biomarker is then performed. The labeling can include at least one amplification technique discussed above. The labeling step, such as with the amplification step, is performed to ensure detectability of the epitope or biomarker when exposed to a second antigen retrieval at or above a given temperature. For example, tyramide signal amplification can be used to detect a first biomarker. During tyramide signal amplification, an activated tyramide-detection moiety conjugate (by way of an enzymatic reaction with horseradish peroxidase) forms a covalent bond with a tyrosine located at or near the first biomarker. The covalent bond is not broken during the second antigen retrieval step, thereby allowing for detection of the first biomarker which could typically be denatured during the second antigen retrieval at or above the given temperature. A second antigen retrieval is then performed at approximately 50-110° C., including at 80-110° C. or, more specifically, at 100° C. The second antigen retrieval is generally performed at a higher temperature than the first antigen retrieval. The second antigen retrieval step is performed on or for an epitope or biomarker which is renatured (or more optimally renatured) at a temperature which can denature at least the first biomarker, as noted above. Labeling of at least one biomarker is then performed. The labeling can include at least one amplification technique discussed above. It should be noted, however, that when antigen retrieval is performed above 100° C., a reagent can be added to increase the boiling point of the sample, thereby reducing or eliminating any damage to the sample. The reagent can include, but is not limited to, a glycol-based solution (e.g., propylene glycol, ethylene glycol, polyethylene glycol), glycerol or a glycerol-based solution, a solution including at least one ionic compound (e.g., a salt solution), or the like. In one embodiment, no intervening or intermediary step is performed between the labeling step and the second antigen retrieval step. In one embodiment, at least one wash step is performed between the labeling step and the second antigen retrieval step.

For example, a sample undergoes a first antigen retrieval process at 50-90° C., 50-85° C., or 70° C. CD45, a granulocyte marker (CD11b, CD66b, or CD15), and an endothelial cell marker (CD105, CD31, or CD144) then undergo labeling. In one embodiment, the labeling incorporates an amplification technique (e.g. horseradish peroxidase and tyramide). The sample then undergoes a second antigen retrieval process at 50-110° C., 80-100° C., or 100° C. Labeling of cytokeratin, EpCAM, a mesenchymal biomarker, and nuclear staining is then performed, such that cytokeratin, EpCAM, and the mesenchymal biomarker incorporated multiple haptens, as discussed above. In this example, the granulocyte marker can be denatured above 90° C. The first antigen retrieval step is performed at 50-90° C. Then, using tyramide signal amplification, the granulocyte marker is labeled. The CD45 and the endothelial cell marker can also be labeled with by tyramide signal amplification. The tyramide signal amplification allows for subsequent detection because the second biomarker, such as vimentin, requires antigen retrieval performed at a temperature above 90° C.

It may be desirable to perform antigen retrieval on a plurality of biomarkers, wherein each biomarker is to be retrieved or unmasked at different temperatures. Starting with the lowest temperature-dependent antigen retrieval step and progressing, ultimately, to the highest temperature-dependent antigen retrieval step. This allows for antigen retrieval of different biomarkers with at least one different antigen retrieval condition.

Some biomarkers or epitopes, for example, can be denatured by antigen retrieval processes where the temperature is greater than or equal to about 80° C. The HRP-tyramide amplification results in activated tyramide, via an enzymatic reaction. The activated tyramide (which is bound to a detection moiety) is deposited in the vicinity of the HRP-biomarker site and forms covalent bonds with particular proteins in the area of deposition. The covalent bonds between the activated tyramides and the proteins are not affected by increased temperatures which may occur in or are required by subsequent antigen retrieval processes, thereby allowing for detection even with subsequently elevated temperatures.

Selective Labeling

In one embodiment, a target or non-target analyte can have a biomarker which is both intracellular and extracellular. In one embodiment, the ratio of one biomarker to another biomarker can be of clinical utility. In one embodiment, it may be desirable to only label or preferentially label one of the intracellular epitope of the biomarker or the extracellular epitope of the biomarker.

In one embodiment, such as where the target analyte (and/or non-target analyte, where appropriate or desirous) has been permeabilized and has both an intracellular epitope and an extracellular epitope, it can be desirous to only label the extracellular epitope of the biomarker. An antigen retrieval step is performed at 70-110° C., and typically at 70-90° C. Labeling is then performed using at least one stain including an affinity molecule directed to the biomarker linked via a linker to a detection moiety. In one embodiment, the detection can be a quantum dot. In one embodiment, the quantum dot has a diameter that is greater than or equal to 2 nanometers. In one embodiment, the quantum dot has a shell that is hydrophilic (e.g., polyethylene glycol (PEG)) or hydrophobic (e.g., a linker containing an alkane chain of at least four carbon atoms). In one embodiment, the quantum dot does not have a shell. In one embodiment, the detection moiety can be an organic fluorophore. In one embodiment, the organic fluorophore can have a molecule weight of at least at least 1 kD, including, without limitation, at least 10 kD, at least 25 kD, at least 50 kD, at least 75 kD, at least 100 kD, at least 150 kD, at least 200 kD, at least 250 kD, at least 300 kD, at least 340 kD, at least 350 kD, at least 500 kD, and at least 750 kD. The linker can be hydrophilic (e.g., polyethylene glycol (PEG)) or hydrophobic (e.g., a linker containing an alkane chain of at least four carbon atoms). For example, the affinity molecule, the hydrophilicity of the linker, and the size of the quantum dot directs the stain to the extracellular epitope of the biomarker and inhibits permeation of the stain across the plasma membrane. Therefore, despite permeabilization of the target analyte, the stain preferentially labels the extracellular epitope of the biomarker, rather than the intracellular epitope. As a more specific example, a stain including a vimentin antibody is linked to QD800 with a PEG linker is added to a sample. A cell, having been permeabilized, can include an intracellular epitope of vimentin and an extracellular epitope of vimentin. However, the characteristics of the stain, as noted above (i.e., hydrophilicity of the linker and size of the quantum dot) are selected to induce preferential labeling of the extracellular epitope.

It should be noted that, despite the method and stain used, some of the stain can label the different epitope of the biomarker than the one desired. However, the amount is negligible.

Algorithm

In one embodiment, after imaging, the detector transmits the data back to the computer or is retained within the scanner. The image data may then be compiled into images, processed and analyzed by a computer or associated software or programs, whereby the target analyte may be characterized, such as by biomarkers present, morphology, clustering, and/or the like. The images formed due to the emission lights may be overlaid when a plurality of fluorescent probes, having bound themselves to the target analyte, are excited and emit light. The computer or scanner may then implement a non-transitory computer-readable medium process to analyze and process the data. The non-transitory computer-readable medium process may detect a candidate object. In one embodiment, target analytes are found using at least one image processing technique, including, but not limited to, thresholding (manual or automatic), template matching, watershedding, cross-correlation, convolutional neural networks, region growing, and edge detection.

Non-Target Analytes

In one embodiment, non-target analytes within the sample can be labeled and detected for removal (i.e. negative marker, dumping, or dump channel) from analysis of the remainder of the sample, such as by image processing and/or algorithm-based methods (i.e. a non-transitory computer-readable medium process). This increases detection of the target analytes by removing the undesired (or non-target) analytes from determination or analysis. For example, stains including affinity molecules for white blood cell biomarkers (such as CD45, a granulocyte marker (CD11b, CD66b, or CD15), and an endothelial cell marker (CD105, CD31, or CD144)) can be used to label and detect the white blood cells so as to be removed from subsequent analysis.

In one embodiment, a single affinity molecule (e.g. antibody) directed to a single biomarker of a non-target analyte can be added to the sample. The single affinity molecule can be directly or indirectly labeled with a detection moiety. An amplification technique can also be implemented.

In one embodiment, a plurality of affinity molecules directed to a plurality of biomarkers of a non-target analyte can be added to the sample. The plurality of affinity molecules can be directly or indirectly labeled with a detection moiety. In one embodiment, each affinity molecule of the plurality of affinity molecules is labeled with a different detection moiety. In one embodiment, at least two affinity molecules of the plurality of affinity molecules are labeled with either: (1) detection moieties providing a signal in the same channel (e.g., a first affinity molecule is bound to or interacted with Alexa 488 and a second affinity molecule is bound to or interacted with QD500), or (2) the same detection moiety (e.g., the affinity molecules are bound to or interacted with Alexa 488). At least one amplification technique can also be implemented for one or more of the biomarkers.

In one embodiment, the non-target analyte can express the mesenchymal cell marker.

Biological Application

Figure 2:
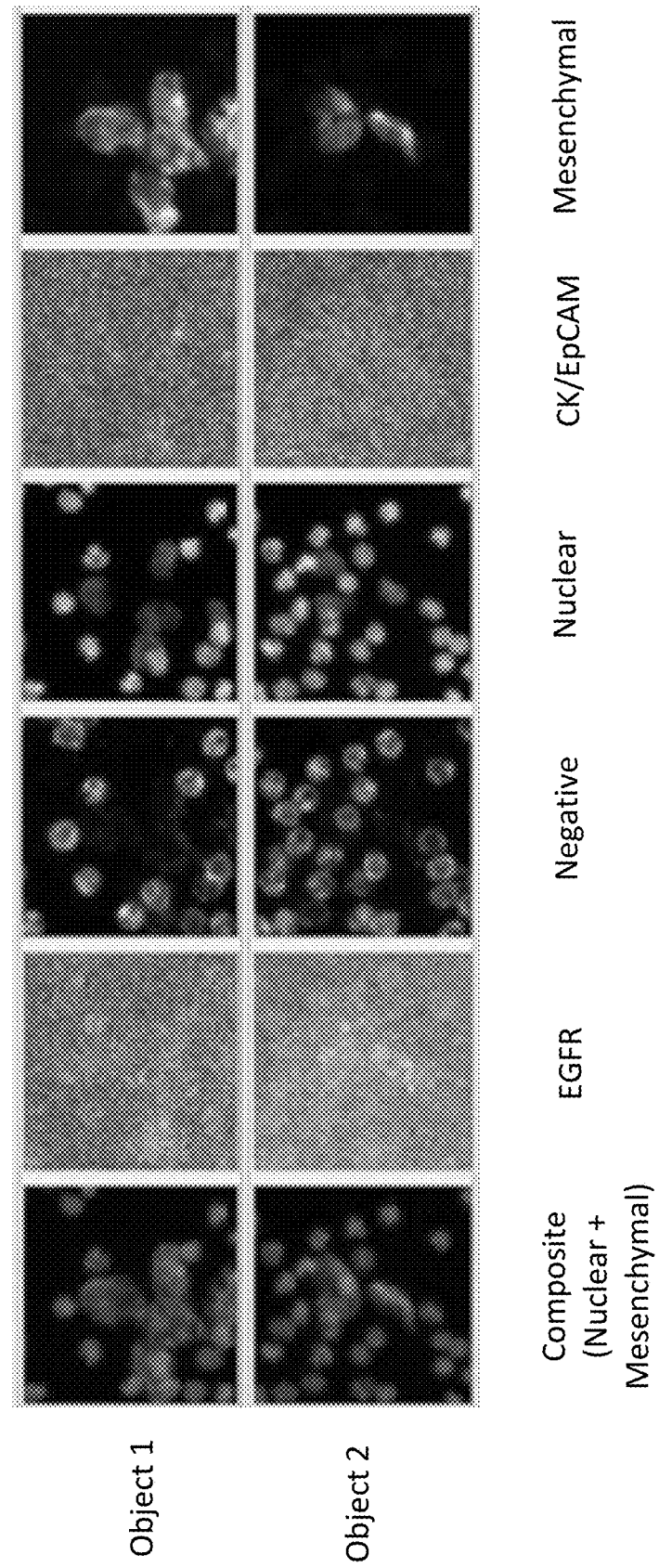
FIG. 2 shows example images for example objects.

FIG. 2 shows example images for objects, such that the term "object" or "candidate object" are terms (which are interchangeable) used to describe a target analyte or non-target analyte before performing analysis and/or scoring used to determine whether the object is a target analyte or non-target analyte. FIG. 2 shows labeled biomarkers (columns) of the various objects (rows).

In one embodiment, a process, as discussed below, incorporates a plurality of sub-steps (i.e. multiplexing, amplification, cyclic labeling, antigen retrieval, non-target analyte dumping, etc.) into the general method. The general method can incorporate any number of sub-steps described herein. The incorporation of these sub-steps allows for the detection of a target analyte having a given definition (for example, a circulating tumor cell that is (EPCAM+ or CK+)/CD45−/nuclear+) and/or a target analyte which does not fall within the given definition (for example, (EPCAM or CK)+/mesenchymal+ or (EPCAM or CK)−/mesenchymal+). In one embodiment, confirmation of these target analytes is done by sequencing.

1. Fix sample
   a. 1 hour in 10% neutral buffered formalin
2. Neutralize with buffer
   b. Tris buffered saline
3. Load onto autostainer or perform manually
4. (Optional) First pre-treatment, such as to eliminate any peroxidase or peroxidase-like compounds on or within the sample
   a. Hydrogen peroxide solution
      i. Includes sodium stannate and Target Retrieval Solution (Dako #51699)
5. First antigen retrieval
   a. Performed at 50-110° C.
      i. Performed at 50-85° C.
      ii. Performed at 70° C.
   b. Include antigen retrieval solution
      i. Such as Ventana CC1
6. Add at least one affinity molecule a. Primary antibody
    i. CD45
    ii. CD11b, CD66b, or CD15
    iii. CD105, CD31, or CD144
7. Perform amplification for the at least one biomarker
  a. Add (secondary) antibody-horseradish peroxidase conjugate to bind to or interact with the at least one antibody added in Step 6
  b. Add tyramide-detection moiety conjugate to interact with the (secondary) antibody-horseradish peroxidase conjugate added in Step 7(a)
8. (Optional) Second pre-treatment, such as to eliminate any peroxidase or peroxidase-like compounds on or within the sample
  a. Hydrogen peroxide solution
    i. Includes sodium stannate and Target Retrieval Solution (Dako #51699)
9. (Optional) At least one wash
10. Second antigen retrieval
  a. Performed at 50-110° C.
    i. Performed at 80-110° C.
    ii. Performed at 100° C.
  b. Include antigen retrieval solution
    i. Such as Ventana CC1
11. (Optional) Add another affinity molecule
  a. Primary antibody
    i. At least one of
      1. EGFR; HER2; PSMA; Ki-67; ER; PSA
12. (Optional) Perform amplification for the at least one biomarker
  a. Add (secondary) antibody-horseradish peroxidase conjugate to bind to or interact with the at least one antibody added in Step 10
  b. Add tyramide-detection moiety conjugate to interact with the (secondary) antibody-horseradish peroxidase conjugate added in Step 11(a)
13. Add at least one more affinity molecule
  a. First positive marker-first hapten
    i. CK-DIG
  b. Second positive marker-first hapten
    ii. EpCAM-DIG
  c. Mesenchymal marker-second hapten
    i. Fibronectin-biotin
    ii. Vimentin-biotin
    iii. N-cadherin-biotin
  d. Nuclear stain
    i. Sytox
14. Add first anti-hapten-detection moiety conjugate
  a. Anti-DIG-Alexa 647
15. Add second anti-hapten or second hapten complementary molecule
  a. Avidin-QD800
    i. Streptavidin-QD800
16. Image or detect at least one detection moiety When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

What is claimed is:

1. A method of detecting one or more biomarkers in a sample or fraction thereof, the method comprising:
   providing the sample or fraction thereof;
   performing a first antigen retrieval on the sample or fraction thereof at 50-90° C. to unmask a desired epitop or biomarker;
   labeling at least one biomarker of the sample or fraction thereof;
   performing a second antigen retrieval on the sample or fraction thereof at a temperature ranging from a temperature of 80-110° C.; and
   detecting an object expressing the at least one biomarker.

2. The method of claim 1, wherein the first antigen retrieval is performed at 50-85° C.

3. The method of claim 1, wherein the at least one biomarker is CD11b, CD15, CD45, CD66b, CD105, or CD144.

4. The method of claim 1, wherein the labeling step comprises labeling the plurality of biomarkers with a plurality of stains, wherein each stain comprises a detection moiety, and wherein the detection moieties of the plurality of stains are in the same channel or have the same emission wavelength.

5. The method of claim 4, wherein the plurality of biomarkers comprises a white blood cell marker, a granulocyte marker, and an endothelial cell marker.

6. The method of claim 4, wherein the detection moieties of the plurality of stains are in the same channel or have the same emission wavelength.

7. The method of claim 1, wherein the first antigen retrieval is performed at 50-80° C.

8. The method of claim 1, wherein the second antigen retrieval is performed at 90-100° C.

9. The method of claim 1, wherein the labeling step further comprises an amplifying step.

10. The method of claim 1, wherein the labeling step causes a covalent bond to be formed between the sample or fraction thereof and a detection moiety.

11. The method of claim 1, further comprising:
    labeling at least one other biomarker with at least one stain,
    wherein the labeling of the at least one other biomarker is performed after the second antigen retrieval.

12. The method of claim 11, the detecting step further comprising detecting the at least one other stain.

13. The method of claim 1, further comprising:
    labeling a second plurality of biomarkers of the sample or fraction thereof,
    wherein labeling the second plurality is performed after the second antigen retrieval.

14. A method, comprising:
    providing a sample or a fraction thereof;

adding, to the sample or fraction thereof, a first plurality of stains directed to a white blood cell marker, a granulocyte marker, and an endothelial cell marker;

adding, to the sample or fraction thereof, a stain directed to a mesenchymal cell marker after having performed at least one antigen retrieval; and detecting at least one target analyte, wherein the at least one target analyte expresses the mesenchymal cell marker, and wherein the at least one target analyte does not express any one of the white blood cell marker, the granulocyte marker, and the endothelial cell marker.

15. The method of claim 14, wherein the detection moiety of the mesenchymal cell marker stain is in a different channel than the detection moieties of the first plurality of stains.

16. The method of claim 15, wherein the detecting step also detects at least one non-target analyte expressing at least one biomarker to which at least one stain of the first plurality of stains is directed.

17. The method of claim 14, wherein the detection moieties of the first plurality of stains emit wavelengths in the same channel.

18. The method of claim 14, wherein the first adding step further comprises amplifying a signal generated by at least one of the stains.

19. The method of claim 14, further comprising performing a first antigen retrieval on the sample or fraction thereof at 50-90° C., wherein the first antigen retrieval step is performed before the first adding step.

20. The method of claim 14, further comprising performing a second antigen retrieval on the sample or fraction thereof at a temperature performing a second antigen retrieval on the sample or fraction thereof at a temperature ranging from a temperature of 80-110° C., wherein the second antigen retrieval step is performed before the second adding step.

21. The method of claim 14, wherein the target analyte is a mesenchymal cell.

22. The method of claim 21, wherein the non-target analyte is a white blood cell or an endothelial cell.

23. The method of claim 14, wherein the granulocyte marker is CD11b, CD66b, or CD15.

24. The method of claim 23, wherein the endothelial cell marker is CD31, CD105, or CD144.

25. The method of claim 14, wherein the mesenchymal cell marker is vimentin, fibronectin, or N-cadherin.

26. The method of claim 14, wherein the second adding step further comprises amplifying a signal generated by at least one of the stains.

27. The method of claim 14, wherein the detecting step further detects at least one non-target analyte expressing:

at least one of the white blood cell marker, the granulocyte marker, or the endothelial cell marker, and the mesenchymal cell marker.

\* \* \* \* \*